United States Patent [19]
Ellis et al.

[11] Patent Number: 5,998,388
[45] Date of Patent: Dec. 7, 1999

[54] ADENOSINE DERIVATIVES

[75] Inventors: Frank Ellis, Lutan; Stephen Swanson, Ware; Richard Peter Charles, Clifton; Brian Cox, Shefford; Andrew Michael Kenneth Pennell, London; Colin David Eldred, Hertford, all of United Kingdom

[73] Assignee: Glaxo Wellcome Inc., Research Triangle Park, N.C.

[21] Appl. No.: 09/180,442

[22] PCT Filed: May 13, 1997

[86] PCT No.: PCT/EP97/02403

§ 371 Date: Nov. 6, 1998

§ 102(e) Date: Nov. 6, 1998

[87] PCT Pub. No.: WO97/43300

PCT Pub. Date: Nov. 20, 1997

[30] Foreign Application Priority Data

May 14, 1996 [GB] United Kingdom .................... 9610031

[51] Int. Cl.⁶ ............................. A61K 31/70; C07H 19/16
[52] U.S. Cl. ................... 514/46; 536/27.62; 536/27.63; 536/27.7
[58] Field of Search ........................... 514/46; 536/27.62, 536/27.63, 27.7

[56] References Cited

U.S. PATENT DOCUMENTS

| | | | |
|---|---|---|---|
| 5,219,840 | 6/1993 | Gadient et al. | 514/46 |
| 5,430,027 | 7/1995 | Knutsen | 514/46 |
| 5,498,605 | 3/1996 | Jacobson et al. | 514/46 |
| 5,688,774 | 11/1997 | Jacobson et al. | 514/46 |
| 5,773,423 | 6/1998 | Jacobson et al. | 514/45 |

FOREIGN PATENT DOCUMENTS

| | | |
|---|---|---|
| 94/02497 | 2/1994 | WIPO . |
| 94/14832 | 7/1994 | WIPO . |
| 95/07921 | 3/1995 | WIPO . |
| 97/33591 | 9/1997 | WIPO . |

OTHER PUBLICATIONS

Andersen et al., "Synthesis of N6–Aryl–2–methyladenosides", Acta Chemica Scandinavica, Ser. B41(6): 473–475, 1987.

Journal of the Chinese Chemical Society, vol. 38, No. 3, Jun. 1991, pp. 289–292, XP002038762 A.F. Sayed Ahmed et al: "Synthesis of some antimicrobial purine nucleoside derivatives." See the whoe document.

Journal of Medicinal Chemistry, vol. 35, No. 12, 1992, Washington US, pp. 2253–2260, XP002038763 T.Abiru et al: "Nucleosides and nucleotides. 107. 2–(cycloalkylakynyl)adenosines: adenosine A2 receptor agonists with potent antihypertensive effects." See the whole document.

Chemical and Pharmaceutical Bulletin, vol. 25, No. 10, 1977, Tokyo JP, pp. 2482–2489, XP002038764 M. Kaneko et al: "Synthesis of N6–or 8–substituted 9–(beta–D–arabino-furanosyl)–adenines and their antiviral activities against Herpes Simplex and Vaccinia viruses." See the whole document.

Patent Abstracts Of Japa vol. 005, No. 035 (C–046), Mar. 5, 1981 & JP 55 160797 A (Ajinomoto Co Inc), Dec. 13, 1980, see abstract.

*Primary Examiner*—Howard C. Lee
*Attorney, Agent, or Firm*—Nixon & Vanderhye

[57] ABSTRACT

This invention relates to novel adenosine derivatives, to processes for their preparation, to pharmaceutical compositions containing them and to their use in medicine.

Thus the invention provides compounds of formula (I) which are agonists at the adenosine A1 receptor.

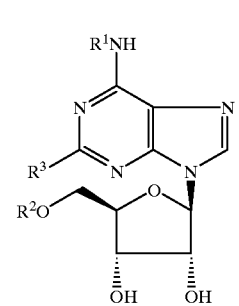

(I)

wherein $R^1$ represents phenyl optionally substituted by one or more substituents selected from halogen, $C_{1-3}$alkyl, trifluoromethyl, nitro, cyano, $-CO_2R^a$, $-CONR^aR^b$, $-COR^a$, $-SOR^c$, $-SO_2R^c$, $-SO_3H$, $-SO_2NR^aR^b$, $-OR^a$, $-NHSO_2R^c$, $-NHCOR^a$ and $-NR^aR^b$, $R^2$ represents a $C_{1-6}$alkyl or $C_{3-6}$alkenyl group; $R^3$ represents $C_{1-3}$alkyl;

$R^a$ and $R^b$ may each independently represent hydrogen or $C_{1-3}$alkyl or, when $-NR^aR^b$ is directly attached to said phenyl, $R^a$ and $R^b$ together with the nitrogen atom may form a –5 or –6 or membered heterocyclic ring optionally containing a second heteroatom selected from oxygen or nitrogen, which second nitrogen heteroatom may optionally be further substituted by hydrogen or $C_{1-3}$alkyl;

$R^c$ represents $C_{1-3}$alkyl;

and salts and solvates thereof, in particular physiologically acceptable salts and solvates thereof.

14 Claims, No Drawings

ADENOSINE DERIVATIVES

This application is a 371 of PCT/EP97/02403 filed on May 13, 1997.

This invention relates to novel adenosine derivatives, to processes for their preparation, to pharmaceutical compositions containing them and to their use in medicine.

Thus the invention provides compounds of formula (I) which are agonists at the adenosine A1 receptor.

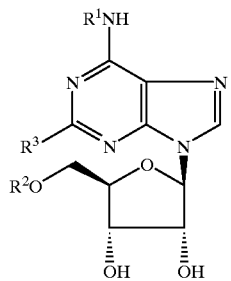

(I)

wherein $R^1$ represents phenyl optionally substituted by one or more substituents selected from halogen, $C_{1-3}$alkyl, trifluoromethyl, nitro, cyano, $-CO_2R^a$, $-CONR^aR^b$, $-COR^a$, $-SOR^c$, $-SO_2R^c$, $-SO_3H$, $-SO_2NR^aR^b$, $-OR^a$, $-NHSO_2R^c$, $-NHCOR^a$ and $-NR^aR^b$;

$R^2$ represents a $C_{1-6}$alkyl or $C_{3-6}$alkenyl group;

$R^3$ represents $C_{1-3}$alkyl;

$R^a$ and $R^b$ may each independently represent hydrogen or $C_{1-3}$alkyl or, when $-NR^aR^b$ is directly attached to said phenyl, $R^a$ and $R^b$ together with the nitrogen atom may form a –5 or –6 or membered heterocyclic ring optionally containing a second heteroatom selected from oxygen or nitrogen, which second nitrogen heteroatom may optionally be further substituted by hydrogen or $C_{1-3}$alkyl;

$R^c$ represents $C_{1-3}$alkyl;

and salts and solvates thereof, in particular physiologically acceptable salts and solvates thereof.

It will be appreciated that when $R^1$ and/or $R^2$ in compounds of formula (I) contain one or more asymmetric carbon atoms the invention includes all diastereoisomers of compounds of formula (I) and mixtures thereof. Otherwise the stereochemical configuration of compounds of the invention is as depicted in formula (I) above.

As used herein, the term "alkyl" means a straight or branched chain alkyl group. Examples of suitable alkyl groups within $R^1$ and $R^2$ include methyl, ethyl, n-propyl, i-propyl, n-butyl, s-butyl, 1-butyl and 3-methylbutyl.

As used herein, the term "$C_{3-6}$alkenyl" means a straight or branched chain alkenyl group containing 3 to 6 carbon atoms. Allyl represents an example of a suitable $C_{3-6}$alkenyl group.

The term "halogen" means fluorine, chlorine, bromine or iodine.

Pharmaceutically acceptable salts of the compounds of formula (I) include those derived from pharmaceutically acceptable inorganic and organic acids. Examples of suitable acids include hydrochloric, hydrobromic, sulphuric, nitric, perchloric, fumaric, maleic, phosphoric, glycollic, lactic, salicylic, succinic, toluene-p-sulphonic, tartaric, acetic, citric, methanesulphonic, formic, benzoic, malonic, naphthalene-2-sulphonic and benzenesulphonic acids. A particularly, suitable pharmaceutically acceptable saft of the compounds of formula (I) is the hydrochloride salt. Other acids such as oxalic, while not, in themselves pharmaceutically acceptable, may be useful as intermediates in obtaining the compounds of the invention and their pharmaceutically acceptable acid addition salts. The solvates may be, for example, hydrates.

When $R^1$ represents a substituted phenyl group the phenyl ring may preferably be substituted by, for example, one or two atoms or groups selected from halogen, hydroxyl, methyl, methoxy, $-CO_2H$, $-CONH_2$ and $-SO_2NH_2$.

More preferred phenyl group substituents within $R^1$ include halogen (in particular, fluorine and chlorine), hydroxyl and methyl. Particularly preferred are halogen (in particular, fluorine or chlorine) and hydroxyl substitution.

$R^1$ preferably represents a group selected from 3-fluoro-4-hydroxyphenyl, 3-chloro-4-hydroxyphenyl, 3-hydroxyphenyl, 4-hydroxyphenyl, 4-hydroxy-2-methylphenyl, 2-fluoro-4-hydroxyphenyl, 3,4-difluorophenyl, 4-fluorophenyl, 3-fluorophenyl, 2-fluorophenyl and 2,4-difluorophenyl.

A particularly preferred $R^1$ group is 3-fluoro-4-hydroxyphenyl.

$R^2$ and $R^3$ preferably independently represent a $C_{1-3}$alkyl group, especially methyl.

It is to be understood that the present invention covers all combinations of particular and preferred groups mentioned hereinabove.

Particular compounds according to the invention include:

N-(3-fluoro-4-hydroxyphenyl)-2,5'-O-dimethyladenosine;

2-Ethyl-N-(3-fluoro-4-hydroxyphenyl)-5'-O-methyladenosine;

N-(3-Chloro-4-hydroxyphenyl)-2-ethyl-5'-O-methyladenosine;

N-(4-Hydroxy-phenyl)-2-methyl-5'-O-methyl-adenosine

N-(4-Hydroxy-2-methyl-phenyl)-2-methyl-5'-O-methyl-adenosine

N-(3-Hydroxy-phenyl)-2-methyl-5'-O-methyl-adenosine

N-(2-Fluoro-4-hydroxy-phenyl)-2-methyl-5'-O-methyl-adenosine

N-(3-Chloro-4-hydroxy-phenyl)-2-methyl-5'-O-methyl-adenosine

2-Methyl-5'-O-methyl-N-[4-(4-methyl-piperazin-1-yl)-phenyl]-adenosine

N-(3,4-Difluorophenyl)-2-methyl-5'-O-methyl-adenosine

2-Methyl-5'-O-methyl-N-(4-methylsulfamoyl-phenyl)-adenosine

N-(4-Hydroxy-3,5-dimethyl-phenyl)-2-methyl-5'-methyl-adenosine

N-(4-Fluoro-phenyl)-2-methyl-5'-O-methyl-adenosine

N-(3-Fluoro-phenyl)-2-methyl-5'-O-methyl-adenosine

N-(4-Hydroxy-3-methyl-phenyl)-2-methyl-5'-O-methyl-adenosine

N-(3-Acetyl4-hydroxy-phenyl)-2-methyl-5'-O-methyl-adenosine

N-(2-Fluoro-phenyl)-2-methyl-5'-O-methyl-adenosine

N-(4-Isopropoxy-phenyl)-2-methyl-5'-O-methyl-adenosine

N-(2-Chloro-phenyl)-2-methyl-5'-O-methyl-adenosine

N-(4-Chloro-2-fluoro-phenyl)-2-methyl-5'-O-methyl-adenosine

N-(2,4-Difluoro-phenyl)-2-methyl-5'-O-methyl-adenosine

N-(2-Fluoro-5-trifluoromethyl-phenyl)-2-methyl-5-methoxy-adenosine

N-(2-Chloro4-fluoro-phenyl)-2-methyl-5'-O-methyladenosine and, pharmaceutically acceptable salts and solvates thereof.

A particularly suitable compound according to the present invention is N-(3-fluoro-4-hydroxyphenyl)-2,5'-O-dimethyladenosine, and pharmaceutically acceptable salts and solvates thereof.

Compounds according to the invention have applicability as inhibitors of lipolysis i.e. they decrease plasma free fatty acid concentrations. The compounds may thus be used in the treatment of hyperlipidaemias. Furthermore, as a consequence of their anti-lipolytic activity, the compounds have the ability to lower elevated blood glucose, insulin and ketone body levels and therefore may be of value in the therapy of diabetes. Since anti-lipolytic agents have hypolipidaemic and hypofibrinogenaemic activity, the compounds may also show anti-atherosclerotic activity. The anti-lipolytic activity of compounds of the invention has been demonstrated by their ability to lower the concentration of non-esterified fatty acids (NEFA) in starved rats dosed orally according to the method described by P. Strong et al. in Clinical Science (1993), 84, 663–669.

In addition to their anti-lipolytic effect, the compounds of the invention may independently affect cardiac function by reducing heart rate and conduction. The compounds may thus be used in the therapy of a number of cardiovascular disorders, for example cardiac arrythmias, particularly following myocardial infarction, and angina.

Furthermore, the compounds of the invention are useful as cardioprotective gents, having applicability in the treatment of ischaemic heart disease. As used herein the term "ischaemic heart disease" includes damage associated with both myocardial ischaemia and reperfusion, for example, associated with coronary artery bypass grafting (CABG), percutaneous translumenal coronary angioplasty (PTCA), cardioplegia, acute myocardial infarction, thrombolysis, stable and unstable angina and cardiac surgery including in particular cardiac transplantation. The compounds of the invention additionally are useful for treating ischaemic damage to other organs. The compounds of the invention may also be valuable in the treatment of other disorders arising as a result of widespread atheromatous disease, for example, peripheral vascular disease (PVD) and stroke.

The compounds may also inhibit renin release and thus be of use in the therapy of hypertension and heart failure. The compounds may also be useful as CNS agents (e.g. as hypnotics, sedatives, analgetics and/or anti-convulsants particularly finding use in the treatment of epilepsy).

In addition, the compounds of the invention may find use in the treatment of sleep apnoea.

The compound of formula (I) and pharmaceutically acceptable acid addition salts thereof are useful as analgesics. They are therefore useful in treating or preventing pain. They may be used to improve the condition of a host, typically of a human being, suffering from pain. They may be employed to alleviate pain in a host. Thus, the compound of formula (I) and its pharmaceutically acceptable acid addition salts may be used as a preemptive analgesic to treat acute pain such as musculoskeletal pain, post operative pain and surgical pain, chronic pain such as chronic inflammatory pain (e.g. rheumatoid arthritis and osteoarthritis), neuropathic pain (e.g. post herpetic neuralgia, trigeminal neuralgia and sympathetically maintained pain) and pain associated with cancer and fibromyalgia. The compound of formula (I) may also be used in the treatment or prevention of pain associated with migraine, tension headache and cluster headaches.

Accordingly, the invention provides a compound of formula (I) or a physiologically acceptable salt or solvate thereof for use in therapy, and in particular in the treatment of human or animal subjects suffering from a condition in which there is an advantage in decreasing plasma free fatty acid concentration, or reducing heart rate and conduction, or whereby the therapy involves the treatment of ischaemic heart disease, peripheral vascular disease or stroke or which subject is suffering from a CNS disorder, sleep apnoea or pain.

In a further aspect, the invention provides a method of treatment of a human or animal subject suffering from a condition in which there is an advantage in decreasing plasma free fatty acid concentration, or reducing heart rate and conduction, or which subject is suffering from or susceptible to ischaemic heart disease, peripheral vascular disease or stroke, or which subject is suffering a CNS disorder or suffering from sleep apnoea or suffering pain, which method comprises administering to the subject an effective amount of a compound of formula (I) or a pharmaceutically acceptable salt or solvate thereof.

In respect of the above mentioned ischaemic treatment, it has been found that according to a particularly unexpected aspect of the present invention, not only does administration of a compound of formula (I) prior to ischaemia provide protection against myocardial infarction, but protection is also afforded if the compound of formula (I) is administered after the ischaemic event and before reperfusion. This means that the methods of the present invention are applicable not only where ischaemia is planned or expected, for example in cardiac surgery, but also in cases of sudden or unexpected ischaemia, for example in heart attack and unstable angina.

It will be appreciated that reference to treatment includes acute treatment or prophylaxis as well as the alleviation of established symptoms.

In yet a further aspect, the invention provides a pharmaceutical composition comprising at least one compound of formula (I) or a pharmaceutically acceptable salt or solvate thereof in association with a pharmaceutical carrier and/or excipient.

In another aspect, the invention provides a pharmaceutical composition comprising, as active ingredient, at least one compound of formula (I) or a pharmaceutically acceptable salt or solvate thereof in association with a pharmaceutical carrier and/or excipient for use in therapy, and in particular in the treatment of human or animal subjects suffering from a condition in which there is an advantage in decreasing plasma free fatty acid concentration, or reducing heart rate and conduction, or which subject is suffering from or susceptible to ischaemic heart disease, peripheral vascular disease or stroke, or which subject is suffering from a CNS disorder, sleep apnoea or pain.

There is further provided by the present invention a process of preparing a pharmaceutical composition, which process comprises mixing at least one compound of formula (I) or a pharmaceutically acceptable salt or solvate thereof, together with a pharmaceutically acceptable carrier and/or excipient.

Compositions according to the invention may be formulated for topical, oral, buccal, parenteral or rectal administration or in a form suitable for administration by inhalation or insufflation. Oral administration is preferred. The compositions may be adapted for sustained release.

For topical administration, the pharmaceutical composition may be given in the form of a transdermal patch, such as an iontophoretic patch or the like.

Tablets and capsules for oral administration may contain conventional excipients such as binding agents, for example mucilage of starch or polyvinylpyrrolidone; fillers, for example, lactose, microcrystalline cellulose or maize-starch; lubricants, for example, magnesium stearate or stearic acid; disintegrants, for example, potato starch, croscarmellose sodium or sodium starch glycollate; or wetting agents such as sodium lauryl sulphate. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, for example, sorbitol syrup, methyl cellulose, or carboxymethyl cellulose; emulsifying agents, for example, sorbitan mono-oleate; non-aqueous vehicles (which may include edible oils), for example, propylene glycol or ethyl alcohol; and preservatives, for example, methyl or propyl p-hydroxybenzoates or sorbic acid. The preparations may also contain buffer salts, flavouring, colouring and sweetening agents (e.g. mannitol) as appropriate.

For buccal administration the compositions may take the form of tablets or lozenges formulated in conventional manner.

The compounds of formula (I) may be formulated for parenteral administration by bolus injection or continuous infusion and may be presented in unit dose form in ampoules, or in multi-dose containers with an added preservative. The compositions may take such forms as suspensions, solutions, or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use.

The compounds of formula (I) may also be formulated as suppositories, e.g. containing conventional suppository bases such as cocoa butter or other glycerides.

A proposed dose of the compounds of the invention for administration to man (of approximately 70 kg body weight) is 1 mg to 2 g, preferably 1 mg to 100 mg, of the active ingredient per unit dose which could be administered, for example, 1 to 4 times per day. It will be appreciated that it may be necessary to make routine variations to the dosage, depending on the age and condition of the patient. The dosage will also depend on the route of administration.

In a yet further aspect the invention also provides for the use of a compound of formula (I) or a pharmaceutically acceptable salt or solvate thereof for the manufacture of a medicament for the treatment of human or animal subjects suffering from a condition in which there is an advantage in decreasing plasma free fatty acid concentration, or reducing heart rate and conduction, or which subject is suffering from or susceptible to ischaemic heart disease, peripheral vascular disease (PVD) or stroke, or which patient is suffering from a CNS disorder, sleep apnoea or pain.

The compounds of formula (I) and physiologically acceptable salts or solvates thereof may be prepared by the processes described hereinafter, said processes constituting a further aspect of the invention. In the following description, the groups $R^1$, $R^2$ and $R^3$ are as defined for compounds of formula (I) unless otherwise stated.

According to a first general process (A), a compound of formula (I) may be prepared by reacting a compound of formula (II)

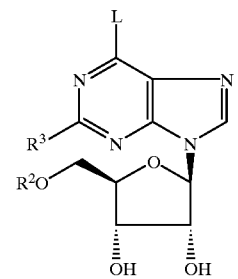

(II)

wherein L represents a leaving group such as a halogen atom (e.g. a chlorine atom) with a compound of formula $R^1NH_2$ or a salt thereof, under basic conditions.

The reaction may conveniently be effected either in the absence or presence of a solvent such as an alcohol (e.g. a lower alkanol such as isopropanol, t-butanol or 3-pentanol), an ether (e.g. tetrahydrofuran or dioxan), a substituted amide (e.g. dimethylformamide), a halogenated hydrocarbon (e.g. chloroform) or acetonitrile, preferably at an elevated temperature (e.g. up to the reflux temperature of the solvent), in the presence of a suitable acid scavenger, for example, inorganic bases such as sodium or potassium carbonate, or organic bases such as triethylamine, diisopropylethylamine or pydridine.

According to another process (B), a compound of formula (I) may be prepared by the deprotection of the corresponding 2',3'-diol-protected compound. Suitable removeable protecting groups include alkylidene, and thus, in one embodiment of process (B), a compound of formula (I) may be prepared from a compound of formula (III)

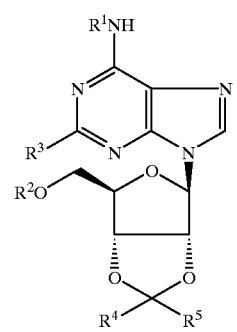

(III)

wherein $R^4$ and $R^5$ are each hydrogen or $C_{1-6}$-alkyl, such as methyl or ethyl, provided that at least one of $R^4$ and $R^5$ is $C_{1-6}$-alkyl. An alkylidene protecting group such as isopropylidene (i.e. $R^4$ and $R^5$ both represent methyl) may conveniently be removed by acid-catalysed hydrolysis, for example using trifluoroacetic or sulphuric acid.

A further process (C) comprises converting a compound of formula (I) into a different compound of formula (I) by modifying the $R^1$ or $R^2$ group therein. Thus, for example, compounds of formula (I) in which $R^2$ represents a $C_{3-6}$alkyl group may conveniently be prepared by the hydrogenation of compounds of formula (I) in which $R^2$ represents a $C_{3-6}$alkenyl group in the presence of a suitable catalyst such as a palladium catalyst (e.g. palladium-on-carbon or palladium oxide-on-carbon) and in an appropriate solvent, for example an alcohol solvent such as ethanol. Compounds of formula (I) in which $R^1$ contains a group —$CONR^aR^b$ may conveniently be prepared from the corresponding compounds of formula (I) in which $R^1$ contains a group $CO_2H$ using conventional methodology.

Compounds of formula (II) may conveniently be prepared by the removal of the alkylidene protecting group from a compound of formula (IV)

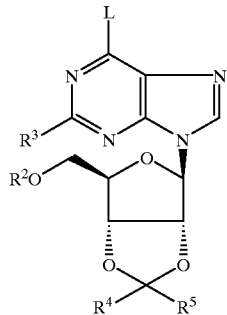

(IV)

wherein $R^4$, $R^5$ and L are as defined previously under the conditions described in process (B) above.

Compounds of formula (IV) may be prepared by treating a compound of formula (V)

wherein $R^4$ and $R^5$ are as defined previously with a halogenating (e.g. chlorinating) agent under conventional conditions. Thus, for example, chlorination may conveniently be effected by treating (V) with phosphorus oxychloride in the presence of an organic base such as 4-dimethylaminopyridine and in a suitable solvent such as acetonitrile at an elevated temperature (e.g. up to the reflux temperature of the solvent).

Compounds of formula (V) may be prepared by alkylation of compounds of formula (VI)

(VI)

wherein $R^4$ and $R^5$ are as defined previously. The alkylation may conveniently be effected by treating a compound of formula (VI) with an alkylating agent $R^2L'$ where L' is a leaving group such as a halogen atom (e.g. a bromine or iodine atom) in the presence of a suitable base such as an alkali metal hydride (e.g. sodium hydride) and an appropriate solvent such as an ether (e.g. dioxan) or dimethylformamide. Alternative alkylating systems will be readily appreciated by those of ordinary skill in the art.

It will be appreciated that $R^1$ or $R^2$ may be converted into a different $R^1$ or $R^2$ grouping as an intermediate step in the overall synthesis of compounds of the invention whereas process (C) hereinabove merely describes interconversion as a final step process.

Compounds of formula (VI) are either known in the art or may be prepared from known compounds using methods analogous to those used in the art to prepare the known compounds of formula (VI).

Compounds of formula (III) may be prepared from compounds of formula (IV) by reacting said compounds of formula (IV) with a compound of formula $R^1NH_2$ or a salt thereof under the conditions described in process (A) above.

According to a further process (D), compounds of formula (II) may be prepared by deprotection of a compound of formula (VII)

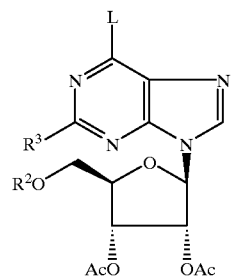

(VII)

wherein L, $R^2$ and $R^3$ are as defined hereinbefore with an amine, e.g. tert-butylamine, in a solvent such as methanol, for example at 0° C.

Compounds of formula (VII) may, in addition be used to produce compounds of formula (I) directly by reaction with the group $R^1NH_2$ either in the absence or presence of a solvent such as an alcohol (e.g. a lower alkanol such as isopropanol, t-butanol or 3-pentanol), an ether (e.g. tetrahydrofuran or dioxan), a substituted amide (e.g. dimethylformamide), a halogenated hydrocarbon (e.g. chloroform) or acetonitrile, preferably at an elevated temperature (e.g. up to the reflux temperature of the solvent), in the presence of a suitable acid scavenger, for example, inorganic bases such as sodium or potassium carbonate, or organic bases such as triethylamine, diisopropylethylamine or pyridine.

This reaction is followed by in situ removal of the acetate protecting groups with an amine such as ammonia in a solvent such as methanol.

Compounds of formula (VII) may be prepared by the reaction of a compound of formula (VIII).

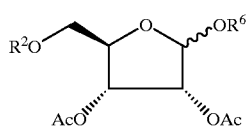

(VIII)

wherein $R^6$ is $C_{1-3}$alkyl, and $R^2$ is defined above, with a compound of formula (IX)

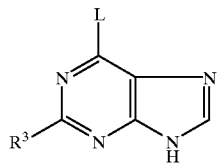

(IX)

wherein L and $R^3$ are defined above.

The reaction is conveniently carried out in a suitable solvent, such as acetonitrile in the presence of a silylating agent such as trimethylsilyl trifluoromethane sulphonate and a base such as diazabicyclo [5.4.0]undec-7-ene (DBU).

Compounds of formula (IX) are either known in the art or may be prepared from known compounds using methods analogous to those used to prepare the known compounds at formula (IX).

Compounds of formula (VIII) are prepared from compounds of formula (X) wherein $R^4$ and $R^5$ are as defined previously by acid catalysed removal of the alkylidine protecting group, e.g. with hydrogen chloride in methanol, followed by in situ acylation for example with acetic anhydride in the presence of a base such as pyridine, in a solvent such as ethyl acetate.

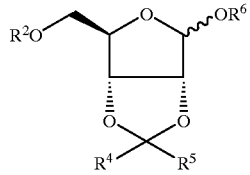

(X)

Compounds of formula (X) are known compounds or prepared by methods analagous to those used in the art to prepare the known compounds of formula X. It will be appreciated by a skilled person that the Acetyl group in any of the compounds above could be replaced with any suitable protecting group, for example, other esters.

Compounds of formulae (II), (III), (IV), (V), (VII) and (VIII) are novel intermediates and form a further aspect of the present invention.

Compounds of the formula $R^1NH_2$ are either known compounds or may be prepared from known compounds using conventional procedures.

Specific optical isomers of a compound of formula (I) may be obtained by conventional methods for example, by synthesis from an appropriate asymmetric starting material using any of the processes described herein, or where appropriate by separation of a mixture of isomers of a compound of formula (I) by conventional means e.g by fractional crystallisation or chromatography.

In the general processes described above, the compound of formula (I) obtained may be in the form of a salt, conveniently into the form of a pharmaceutically acceptable salt. Where desired, such salts may be converted into the corresponding free bases using conventional methods.

Pharmaceutically acceptable acid addition salts of the compounds of formula (I) may be prepared by reacting a compound of formula (I) with an appropriate acid in the presence of a suitable solvent such as acetonitrile, acetone, chloroform, ethyl acetate or an alcohol (e.g. methanol, ethanol or isopropanol). Pharmaceutically acceptable base addition salts may be obtained in an analogous manner by treating a solution of a compound of formula (I) with a suitable base. Pharmaceutically acceptable salts may also be prepared from other salts, including other pharmaceutically acceptable salts of the compounds of formula (I), using conventional methods.

The invention is further illustrated by the following non-limiting Intermediates and Examples. Temperatures are in ° C.

Standard Automated Preparative HPLC Column Conditions & Eluent

Automated preparative high performance liquid chromatography (autoprep.

HPLC) was carried out using a Supelco ABZ+5 μm 100 mm×22 mm i.d column eluted with a mixture of solvents consisting of I) 0.1% formic acid in water and ii) 0.05% formic acid in acetonitrile, the eluent being expressed as the percentage of ii) in the solvent mixture, at a flow rate of 4 ml per minute. Unless otherwise stated the eluent was used as a gradient of 0–95 over 20 minutes.

LC/MS System

The Liquid Chromotography Mass Spectroscopy (LC/MS) system used as an ABZ+PLUS, 3.3 cm×4.6 mm i.d. column eluting with solvents: A–0.1% v/v formic acid+0.077% w/v ammonium acetate in water, and B–95:5 acetonitrile:water+0.05% v/v formic acid. The following gradient protocol was used: 100% A for 0.7 mins; A+B mixtures, gradient profile 0–100% B over 3.5 mins; hold at 100% B for 3.5 mins; return to 0% over 0.3 mins.

Intermediate 1

2.5'-O-Dimethyl-2',3'-O-(1-methylethylidene)inosine[1]

A solution of 2-methyl-2',3'-(1-methylethylidene)inosine[1] (4.0 g) in dry dimethylformamide (31 ml) was added dropwise to an ice-cooled suspension of sodium hydride (60% dispersion in oil, 1.09 g) in dry dimethylformamide (8 ml). The resulting suspension was stirred at room temperature for 2 hours, recooled to 0° and treated with iodomethane (0.82 ml). The reaction mixture was stirred at room temperature for 20 hours, acetic acid (1.54 ml) was added and stirring was continued for a further 24 hours. The solvent was removed under vacuum and the residue was purified by flash chromatography on a silica column (Merck 9385, dichloromethane/methanol/ammonia 97:3:0.5 changing to 95:5:0.5) to give the title compound (1.16 g) as a light brown foam.

T.I.c. silica (dichloromethane/methanol/ammonia 90:10:1) Rf 0.38.

1. A Yamazaki et al., J. Org.Chem. 1967, 32, 3258.

Intermediate 2

1-(6-Chloro-2-methyl-9H-purin-9-yl)-1-deoxy-5-O-methyl-2,3-O-(1-methylethylidene)-b-D-ribofuranose Phosphorus oxychloride (0.8 ml) was added to a mixture of Intermediate 1 (1.16 g) and 4-dimethylaminopyridine (462 mg) in dry acetonitrile (15 ml) which was then stirred at reflux for 2.75 hours. The cooled solution was concentrated under vacuum and the residue was basified using 2N sodium carbonate (75 ml). The aqueous mixture was extracted with ethyl acetate (×2) and the combined organic extracts were dried ($Na_2SO_4$) and concentrated to a brown oil which was purified by flash chromatography on a silica column (Merck 9385, cyclohexane/ethyl acetate 1:1) to give the title compound (436 mg) as a colourless oil.

T.I.c. silica (cyclohexane/ethyl acetate 1:1) Rf 0.29.

Intermediate 3

1-(6-Chloro-2-methyl-9H-purin-9-yl)-1-deoxy-5-O-methyl-b-D-ribofuranose

Ice-cold Intermediate 2 (415 mg) was -treated with an ice-cold mixture of trifluoroacetic add (4.2 ml) and water (0.42 ml) and the reaction mixture was stirred at 0° for 1.5 hours. Excess trifluoroacetic acid was removed under vacuum and the residue was purified by flash chromatography on a silica column (Merck 9385, dichloromethane/methanol/ammonia 130:10:1) to give the title compound (276 mg) as a white solid.

T.l.c. silica (dichloromethane/methanol/ammonia 90:10:1) Rf 0.48.

In an alternative method intermediate 3 was synthesised by the following procedure.

Tert-Butylamine (3.5 ml) was added to a cooled suspension of acetic acid 4R-acetoxy-2R-(6-chloro-2-methyl-purin-9-yl)-5R-methoxymethyl-tetrahydro-furan-3R-yl ester ('intermediate 8') (4.75 g) in methanol (53 ml), and the mixture was stirred at 0° for 1.5 h. The mixture was filtered, and the residue washed with methanol and dried in vacuo at 50° to give the title compound as a white powder (0.9 g). Concentration of the mother liquors in vacuo and trituration of the residue with diisopropyl ether (25 ml) gave further title compound (2.6 g) as a white powder.

Intermediate 4

2-Ethyl-5'-O-methyl-2',3'-O-(1-methylethylidene) inosine

A solution of 2-ethyl-2',3'-O-(1-methylethylidene) inosine[2] (1.11 g) in dry dimethylformamide (25 ml) was added to an ice-cooled suspension of sodium hydride (60% dispersion in oil, 290 mg) in dry dimethylformamide (10 ml) and the resulting suspension was stirred at room temperature for 3 hours. Iodomethane (0.2 ml) was added, stirring was continued for 2 hours, then acetic acid was added and the reaction mixture was stirred at room temperature for 18 hours.

The pale yellow suspension was concentrated under vacuum and the residue was purified (×2) by flash chromatography on a silica column: [A] ( Merck 9385, dichloromethane/ethanol/ammonia 100:8:1) and [B] (Merck 9385, dichloromethane/ethanol/ammonia 200:8:1) to give the title compound (274 mg) as a white foam.

Analysis Found: C, 53.4; H, 6.1 ; N, 15.5; $C_{16}H_{22}N_4O_5 \cdot 0.5H_2O$ Requires: C, 53.5; H, 6.45; N, 15.6%.

2. A Yamazaki et al., J. Org. Chem. 1967, 32, 3258.

Intermediate 5

1-(6-Chloro-2-ethyl-9H-purin-9yl)-1-deoxy-5-O-methyl-2,3-O-(1-methylethylidene)-b-D-ribofuranose Phosphorus oxychloride (1.66 ml) was added to a stirred solution of Intermediate 4 (2.5 g) in dry acetonitrile (50 ml) containing 4-dimethylaminopyridine (0.96 g) and the mixture was stirred at 90° for 4 hours. The cooled solution was concentrated under vacuum to give a brown oil which was cautiously diluted with 8% aqueous sodium bicarbonate (50 ml) then extracted with ethyl acetate (×2). The combined organic extracts were dried ($Na_2SO_4$) and concentrated to an orange oil which was purified by flash chromatography on a silica column (Merck 9385, cyclohexane/ethyl acetate 2:1) to give the title compound (1.75 g) as a yellow gum.

Analysis Found: C, 52.5; H, 5.7; N, 14.9; $C_{16}H_{21}ClN_4O_4$ Requires: C, 52.1; H, 5.7; N, 15.2%.

Intermediate 6

1-(6-Chloro-2-ethyl-9H-purin-9-yl)-1-deoxy-5-O-methyl-b-D-ribofuranose

Ice-cold Intermediate 5 (1.74 g) was treated with an ice-cold mixture of trifluoroacetic acid (18 ml) and water (1.8 ml) and the reaction mixture was stirred at 0 for 1.5 hours. Excess trifluoroacetic acid was removed under vacuum and the residue was purified by repeated (×3) flash chromatography on a silica column (Merck 9385, dichloromethane/methanol/ammonia [A] 100:8:1 [B] 200:8:1 [C] 500:8:1) to give the title compound (1.11 g) as a white solid.

T.l.c. silica (dichloromethane/methanol/ammonia 400:8:1) Rf 0.40.

Intermediate 7

Acetic acid-4R-acetoxy-5-methoxy-2R-methoxymethyl-tetrahydro-furan-3R-yl ester

Acetyl chloride (29.4 ml) was added to methanol (1806 ml), (3aR,4R,6R, 6aR)-4-methoxy-6-methoxymethyl-2,2-dimethyl-tetrahydro-furo[3,4-d][1,3]dioxole(90.3 g) was added, and the mixture was heated under reflux for 5 days, during which time methanol was continuously distilled off and replaced with fresh methanol in order to drive the reaction near to completion. Pyridine (117 ml) was added, and the methanol was replaced by ethyl acetate by distilling off the solvent and replacing with ethyl acetate until the solvent was distilling at 76°. The volume was reduced to 400 ml, the mixture cooled to 22°, acetic anhydride (136 ml) added, and the mixture was stirred at 22° for 16 h. The mixture was poured into saturated aqueous sodium bicarbonate (500 ml), and solid sodium bicarbonate was added until pH>7 was obtained. After stirring for 30 min, the aqueous layer was separated and further extracted with ethyl acetate. The combined organic layers were dried ($MgSO_4$), evaporated in vacuo, and azeotroped with toluene. Distillation at 0.042 mbar gave the title compound as a colourless oil (43.6 g).

TLC $SiO_2$ (isohexane:ethyl acetate 1:1) 2 spots ($\alpha$ and $\beta$ anomers), Rf 0.6, 0.7.

3: Gudmundsson et al; J Med. Chem. (1997) 40(S), 785–793.

Intermediate 8

Acetic acid 4R-acetoxy-2R-(6-chloro-2-methyl-purin-9-yl-5R-methoxymethyl-tetrahydro-furan-3R-yl ester 6-Chloro-2-methyl9H-purine hydrochloride 4 (18.4 g) was added at 20° to a stirred solution of acetic acid 4R-acetoxy-5-methoxy-2R-methoxymethyl-tetrahydro-furan-3R-yl ester (intermediate 7) (20.0 g) in acetonitrile (200 ml). 1,8-diazabicyclo [5.4.0] undec-7-ene (DBU) (34.2 ml) was added in 2 portions, maintaining the temperature at 15+/−50°. After stirring for 5 min at 20°, trimethylsilyl trifluoromethanesulphonate (73.7 ml) was added dropwise over 3 min, maintaining the temperature at 20°. The mixture was warmed to 60° for 2 h, and transferred via cannula into water (400 ml) containing potassium carbonate (84 g). The mixture was extracted with ethyl acetate (4×100 ml), and the organic layers were washed with 0.5M hydrochloric acid (200 ml) and aqueous potassium carbonate, dried ($MgSO_4$), and evaporated in vacuo. The oily residue was purified by chromatography on silica gel, eluting with ethyl acetate, and by recrystallation from ethyl acetate to give the title compound (16.5 g).

TLC $SiO_2$ (Ethyl acetate:cyclohexane 1:1) Rf=0.2

Mass Spectrum m/z 399 [MH+]

4: Robins et al; J. Org. Chem, 1956, 21, 695–696

EXAMPLE 1

N-(3-Fluoro-4-hydroxyphenyl)-2.5'-O-dimethyladenosine

A solution of Intermediate 3 (138 mg), 4-amino-2-fluorophenol (66 mg) and diisopropylethylamine (0.15 ml)

in isopropanol (12 ml) was stirred at reflux for 7 days then allowed to cool to room temperature. The resulting precipitate was collected by filtration, washed with isopropanol then ether and dried under vacuum to give the title compound (119 mg) as a beige powder.

N.m.r. (d6-DMSO) δ9.75 (1H, s), 9.5 (1H, vbrs), 8.42 (1H, s), 7.95 (1H, dd), 7.57 (1H, dt), 6.93 (1H, dd), 5.98 (1H, d), 5.8–5.2 (2H, 2xvbrs), 4.65 (1H, t), 4.19 (1H, t), 4.08 (1H, q), 3.62 (2H, ABX), 3.35 (3H, s), 2.57 (3H, s).

T.l.c. silica (dichloromethane/methanol/ammonia 90:10:1) Rf 0.38.

In an alternative method, 4-amino-2-fluorophenol hydrochloride was used.

EXAMPLE 2

2-Ethyl-N-(3-fluoro-4-hydroxyphenyl)-5'-O-methyladenosine

A solution of Intermediate 6 (370 mg), 4-amino-2-fluorophenol (142 mg) and diisopropylethylamine (0.15 ml) in isopropanol (12 ml) was stirred at reflux for 4.5 days then allowed to cool to room temperature. The resulting precipitate was collected by filtration, washed with isopropanol and dried under vacuum to give the title compound (135 mg) as a grey solid.

N.m.r. (d6-DMSO) δ9.7 (1H, s), 9.5 (1H, brs), 8.4 (1H, s), 7.99 (1H, dd), 7.56 (1H, dt), 6.93 (1H, dd), 5.97 (1H, d), 5.6–5.2 (2H, 2xbrs), 4.69 (1H, brq), 4.2 (1H, brq), 4.05 (1H, q), 3.6 (2H, ABX), 3.3 (3H, s), 2.82 (2H, q) 1.32 (3H, t).

Analysis Found: C, 53.6; H, 5.3, N, 16.3; $C_{19}H_{22}FN_5O_5 \cdot 0.4H_2O$ Requires: C, 53.5; H, 5.4; N, 16.4%.

EXAMPLE 3

N-(3-Chloro-4-hydroxyphenyl)-2-ethyl-5'-O-methyladenosine

A solution of Intermediate 6 (320 mg), 4-amino-2-chlorophenol (150 mg) and diisopropylethylamine (0.2 ml) in isopropanol (12 ml) was stirred at reflux for 24 hours then allowed to cool to room temperature. The resulting precipitate was collected by filtration, washed with isopropanol and dried under vacuum to give the title compound (38 mg) as a grey solid.

Analysis Found: C, 50.35; H, 5.5; N, 15.0; $C_{19}H_{22}ClN_5O_5H_2O$ Requires: C, 50.3; H, 5.3; N, 15.4%.

T.l.c. silica (dichloromethane/methanol/ammonia 90:10:1) Rf 0.46.

EXAMPLES 4–16

Examples 4–16 were prepared from Intermediate 3 by analogous means to Example 1, using various reaction times (18 h–10 days) and stoichiometry depending on the reactivity of the aniline. In examples 15 and 16 the solvent was evaporated after initial mixing of the reagents, and the reaction mixtures were heated as pellets.

EXAMPLE 4

N-4-Hydroxy-phenyl)-2-methyl-5'-O-methyl-adenosine

TLC $SiO_2$ ($CH_2Cl_2$:EtOH:880$NH_3$ 50:8:1) $R_f$=0.6
Mass spectrum m/z 388 [MH$^+$]

EXAMPLE 5

N-(4-Hydroxy-2-methyl-phenyl)-2-methyl-5'-O-methyl-adenosine

TLC $SiO_2$ ($CH_2Cl_2$:EtOH:880$NH_3$ 100:8:1) $R_f$=0.17
Analysis Found: C, 55.9; H, 5.9; N, 16.6.
$C_{19}H_{23}N_5O_5 \cdot 0.5\ H_2O$ requires: C, 55.6; H, 5.9; N, 17.1.

EXAMPLE 6

N-(3-Hydroxy-phenyl)-2-methyl-5'-O-methyl-adenosine

TLC $SiO_2$ ($CH_2Cl_2$:EtOH:880$NH_3$ 100:8:1) $R_f$=0.2
Mass spectrum m/z 388 [MH$^+$]

EXAMPLE 7

N-(2-Fluoro-4-hydroxy-phenyl)-2-methyl-5'-O-methyl-adenosine

TLC $SiO_2$ ($CH_2Cl_2$:EtOH:880$NH_3$ 50:8:1) $R_f$=0.55
Analysis found: C, 51.45; H, 4.9; N, 16.15. $C_{18}H_{20}N_5O_5F \cdot H_2O$ requires; C,51.1; H, 5.2; N, 16.5.

EXAMPLE 8

N-(3-Chloro-4-hydroxy-phenyl)-2-methyl-5'-O-methyl-adenosine

TLC $SiO_2$ ($CH_2Cl_2$:EtOH:880$NH_3$ 50:8:1) $R_f$=0.57
NMR (DMSO)
9.88 δ(1H, brs, CH), 9.70 δ(1H, s, NH), 8.4 δ(1H, s, CH), 8.02 δ(1H, d, AROMATIC CH), 7.7 δ(1H, dd, AROMATIC CH), 6.98 δ(1H, d, AROMATIC CH), 5.98 δ(1H, d, CH), 5.58 δ(1H, brs, OH), 5.3 δ(1H, brs, OH), 4.62 δ(brt, CH), 4.18 δ(1H, brt, CH), 4.04 δ(1H, q, CH), 3.7–3.5 δ(2H, m, CH), 3.30 δ(3H,s, —OMe), 2.5 δ(3H, s, —Me).

EXAMPLE 9

2-Methyl-5'-O-methyl-N-[4-(4-methyl-piperazin-1-yl)-phenyl]-adenosine

Mass spectrum m/z 470 [MH$^+$]
TLC $SiO_2$ ($CH_2Cl_2$:MeOH 9:1) $R_f$=0.17

EXAMPLE 10

N-(3,4-Difluoro-phenyl)-2-methyl-5'-O-methyl-adenosine

TLC $SiO_2$ ($CH_2Cl_2$:EtOH:880$NH_3$ 100:10:1) $R_f$=0.4
Mass spectrum m/z 408 [MH$^+$]

EXAMPLE 11

2-Methyl-5'-O-methyl-N-4-methylsulfamoyl-phenyl)-adenosine

TLC $SiO_2$ ($CH_2Cl_2$:EtOH:880$NH_3$ 100:12:1.5) $R_f$=0.29
Mass spectrum m/z 465 [MH$^+$]

EXAMPLE 12

N-(4-Hydroxy-3,5-dimethyl-phenyl)-2-methyl-5'-O-methyl-adenosine

TLC $SiO_2$ ($CH_2Cl_2$:EtOH:880$NH_3$ 100:12:1.5) $R_f$=0.34
Mass spectrum m/z 416 [MH$^+$]

EXAMPLE 13

N-(4-Fluoro-phenyl)-2-methyl-5'-O-methyl-adenosine

TLC $SiO_2$ ($CH_2Cl_2$:EtOH:880$NH_3$ 100:10:1) $R_f$=0.34
Mass spectrum m/z 390 [MH$^+$]

EXAMPLE 14

N-(3-Fluoro-phenyl)-2-methyl-5'-O-methyl-adenosine

TLC SiO$_2$ (CH$_2$Cl$_2$:EtOH:880NH$_3$ 200:5:1) Rf =0.18
Mass spectrum (electrospray) m/z 390.1571 [MH$^+$]

EXAMPLE 15

N-(4-Hydroxy-3-methyl-phenyl)-2-methyl-5'-O-methyl-adenosine

Mass spectrum m/z 402 [MH$^+$]
NMR (CD$_3$OD) 8.42 δ(1H, s, CH), 7.25 δ(1H, brs, AROMATIC CH), 7.20 δ(1H, brd, AROMATIC CH), 6.82 δ(1H, d, AROMATIC CH), 6.1 δ(1H, d, CH), 4.65 δ(1H, t, CH), 4.35 δ(1H, t, CH), 4.20 δ(1H, m, CH), 3.8–3.5 δ(2H, m, CH$_2$), 3.42 δ(3H, s, —Ome), 2.60 δ(3H, s, —Me), 2.22 δ(3H, s, —Me).

EXAMPLE 16

N-(3-Acetyl-4-hydroxy-phenyl)-2-methyl-5'-O-methyl-adenosine

Mass spectrum m/z 430 [MH$^+$]
NMR (CD$_3$OD) 8.42 δ(1H, brd, AROMATIC CH), 8.4 δ(1H, s, CH), 7.75 δ(1H, dd, AROMATIC CH), 7.0 δ(1H, d, AROMATIC CH), 6.08 δ(1H, d, CH), 4.57 δ(1H t, CH), 4.34 δ(1H, t, CH), 4.20 δ(1H, m, CH), 3.8–3.60 δ(2H, m, CH$_2$), 3.42 δ(3H, s, —OMe), 2.68 δ(3H, s, —COMe), 2.60 δ(3H, s, —Me)

EXAMPLE 17

N-(2-Fluoro-phenyl)-2-methyl-5'-O-methyl-adenosine

Acetic acid 4R-acetoxy-2R-(6-chloro-2-methyl-purin-9-yl)-5R-methoxymethyl-tetrahydro-furan-3R-yl ester (intermediate 8) (50 mg, 0.125 mmol) was added to isopropanol (5 ml), N,N-diisopropylethylamine (0.75 mmol, 0.131 ml) and 2-fluoroaniline (0.049 ml; 0.501 mmol). The reaction mixture was heated under reflux with stirring under nitrogen for 8 days. On cooling to room temperature (22°), methanolic ammonia (6 ml) was added to the reaction mixture, the solution was shaken and left standing at 22° for 2 days. The solvent was evaporated under a stream of nitrogen, and the residue purified by solid phase extraction (5 g Varian Bondelut cartridge, aminopropyl bonded phase). Further purification by automated HPLC gave the title compound (23 mg).

TLC SiO$_2$ (CH$_2$Cl$_2$:MeOH 9:1) R$_f$=0.33
Mass spectrum m/z 390 [MH+]

EXAMPLES 18–23

Examples 18–23 were prepared by analagous methods to Example 17 except that for Examples 19–23, 3-pentanol was used as the solvent at 115° C.

EXAMPLE 18

N-(4-isopropoxy-phenyl)-2-methyl-5'-O-methyl-adenosine

TLC SiO$_2$ (CH$_2$Cl$_2$:MeOH 9:1) R$_f$=0.30
Mass spectrum m/z 430 [MH$^+$]

EXAMPLE 19

N-(2-Chloro-phenyl)-2-methyl-5'-O-methyl-adenosine accurate mass m/z (found)=406.127462
(calc.)=406.128207
LC/MS R$_1$=4.55 min

EXAMPLE 20

N-(4-Chloro-2-fluoro-phenyl)-2-methyl-5'-O-methyl-adenosine accurate mass m/z (found)=424.119540
(calc.) 424.118785
LC/MS R$_1$=4.70 min

EXAMPLE 21

N-(2,4-Difluoro-phenyl)-2-methyl-5'-O-methyl-adenosine accurate mass m/z (found)=408.147738
(calc.)=408.148336
LC/MS R$_t$=3.80 min

EXAMPLE 22

N-(2-Fluoro-5-trifluoromethyl-phenyl)-2-methyl-5'-methoxy-adenosine accurate mass m/z (found)=458.144475
(calc.)=458.145142
LC/MS R$_t$=4.24 min

EXAMPLE 23

N-(2-Chloro4-fluoro-phenyl)-2-methyl-5'-O-methyl-adenosine accurate mass m/z (found)=424.119387
(calc.)=424.118785
LC/MS R$_t$=4.02 min Resorter Gene Experiments Agonist activity was measured in Chinese hamster ovary (CHO) cells containing the CRE/SPAP/HYG (CRE=cyclic AMP response element; HYG=hygromycin; SPAP=secreted placental alkaline phosphatase) reporter gene, which upon stimulation of CAMP levels produced SPAP. A cell line was used, which stably co-expresses the human adenosine A1 receptor. Cells were plated out in 96-well plates in culture medium and incubated at 37° C. for 1 hour. For measurement of potency, agonists were added to the appropriate wells at a concentration range of approximately $10^{-10}$–$10^{-5}$M. 15 Min later, cAMP levels were stimulated by addition of a maximal concentration of forskolin. All cells were then incubated for a further 5 hours at 37° C., and cooled to room temperature, after which a substrate for the phosphatase (para-nitrophenol phosphate,pNPP), which is broken down to a coloured reagent) was then added and the 96-well plates are read in a plate reader. From these readings, the concentration-dependence of the inhibition by the agonist of forskolin-stimulated SPAP production, can be calculated. One of the agonists tested on each 96-well plate was the standard non-selective agonist, N-ethylcarboxamidoadenosine (NECA), and the potency of all test agonists is expressed relative to that of the NECA standard.

(ECR=equipotent concentration ratio relative to NECA= 1).

TABLE 2

Biological data; A1 Receptor Gene Assay ECR

| Example No. | Reporter Gene Assay ECR |
|---|---|
| 1 | 12.1 |
| 4 | 37.4 |
| 5 | 4.2 |
| 7 | 4.0 |
| 8 | 11.3 |
| 10 | 9.6 |
| 11 | 92.5 |
| 12 | 154.3 |
| 13 | 26.5 |
| 14 | 40.7 |
| 15 | 206 |
| 16 | 293 |
| 17 | 57.8 |
| 18 | 122.3 |

We claim:

1. An A1 agonist compound of formula (I)

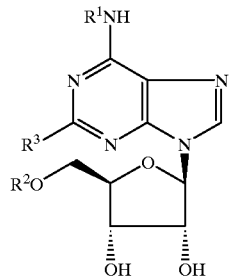

(I)

wherein $R^1$ represents phenyl optionally substituted by one or more substituents selected from halogen, $C_{1-3}$alkyl, trifluoromethyl, nitro, cyano, —$CO_2R^a$, —$CONR^aR^b$, —$COR^a$, —$SOR^c$, —$SO_2R^c$, —$SO_3H$, —$SO_2NR^aR^b$, —$OR^a$, —$NHSO_2R^c$, —$NHCOR^a$ and —$NR^aR^b$;

$R^2$ represents a $C_{1-6}$alkyl or $C_{3-6}$alkenyl group;

$R^3$ represents $C_{1-3}$alkyl;

$R^a$ and $R^b$ may each independently represent hydrogen or $C_{1-3}$alkyl or, when —$NR^aR^b$ is directly attached to said phenyl, $R^a$ and $R^b$ together with the nitrogen atom may form a –5 or –6 or membered heterocyclic ring optionally containing a second heteroatom selected from oxygen or nitrogen, which second nitrogen heteroatom may optionally be further substituted by hydrogen or $C_{1-3}$alkyl;

$R^c$ represents $C_{1-3}$alkyl;

and salts and solvates thereof.

2. A compound according to claim 1 wherein $R^1$ represents a phenyl optionally substituted by one or two atoms or group selected from halogen, hydroxyl, methyl, methoxy, $CO_2H$, —$CONH_2$ and $SO_2NH_2$.

3. A compound according to claim 2 wherein the phenyl group substituents are halogen, hydroxyl and methyl.

4. A compound according to claim 3 wherein the phenyl group substituents are halogen and hydroxyl.

5. A compound according to claim 1 wherein $R^1$ represents a group selected from 3-fluoro-4-hydroxy phenyl, 3chloro-4-hydroxyphenyl, 3-hydroxyphenyl, 4-hydroxyphenyl, 4-hydroxy-2-methylphenyl, 2-fluoro4, hydroxyphenyl, 3,4-difluorophenyl, 4-fluorophenyl, 3-fluorophenyl, 2-fluorophenyl and 2,4-difluorophenyl.

6. A compound according to claim 5 wherein $R^1$ is 3-fluoro4-hydroxy phenyl.

7. A compound according to claim 1 wherein $R^2$ and $R^3$ independently represent a $C_{1-4}$alkyl group.

8. A compound according to claim 7 where $R^2$ and $R^3$ independently represent methyl.

9. A compound according to claim 1 which is;

N-(3fluoro-4-hydroxyphenyl)-2,5'-O-dimethyladenosine;

2-Ethyl-N-(3-fluoro4-hydroxyphenyl)-5'-O-methyladenosine;

N-(3-Chloro-4-hydroxyphenyl)-2-ethyl-5'-O-methyladenosine;

N-(4-Hydroxy-phenyl)-2-methyl-5'-O-methyl-adenosine;

N-(4-Hydroxy-2-methyl-phenyl)-2-methyl-5'-O-methyl-adenosine;

N-(3-Hydroxy-phenyl)-2-methyl-5'-O-methyl-adenosine;

N-(2-Fluoro4-hydroxy-phenyl)-2-methyl-5'-O-methyl-adenosine;

N-(3-Chloro-4-hydroxy-phenyl)-2-methyl-5'-O-methyl-adenosine;

2-Methyl-5'-O-methyl-N-[4-(4-methyl-piperazin-1-yl)-phenyl]-adenosine;

N-(3,4-Difluoro-phenyl)-2-methyl-5'-O-methyl-adenosine;

2-Methyl-5'-O-methyl-N-4-methylsulfamoyl-phenyl)-adenosine;

N-(4-Hydroxy-3,5-dimethyl-phenyl)-2-methyl-5'-O-methyl-adenosine;

N-(4-Fluoro-phenyl)-2-methyl-5'-O-methyl-adenosine;

N-(3-Fluoro-phenyl)-2-methyl-5'-O-methyl-adenosine;

N-(4-Hydroxy-3-methyl-phenyl)-2-methyl-5'-O-methyl-adenosine;

N-(3-Acetyl-4-hydroxy-phenyl)-2-methyl-5'-O-methyl-adenosine;

N-(2-Fluoro-phenyl)-2-methyl-5'-O-methyl-adenosine;

N-(4-Isopropoxy-phenyl)-2-methyl-5'-O-methyl-adenosine;

N-(2-Chloro-phenyl)-2-methyl-5'-O-methyl-adenosine;

N-(4-Chloro-2-fluoro-phenyl)-2-methyl-5'-O-methyl-adenosine;

N-(2,4-Difluoro-phenyl)-2-methyl-5'-O-methyl-adenosine;

N-2-Fluoro-5-trifluoromethyl-phenyl)-2-methyl-5'-methoxy-adenosine; or

N-(2-Chloro-4-fluoro-phenyl)-2-methyl-5'-O-methyl-adenosine.

10. A pharmaceutical formulation comprising a compound according to claim 1 together with one or more pharmaceutically acceptable carriers.

11. A process of preparing a pharmaceutical formulation comprising a compound according to claim 1 together with one or more pharmaceutical carriers, which process comprises mixing said compound together with said one or more carriers.

12. A method of treating human or animal subject suffering from a condition in which there is an advantage in decreasing plasma free fatty acid concentration, reducing heart rate and conduction, or which subject is suffering from or is susceptible to ischemic heart disease, peripheral vascular disease or stroke, or which subject is suffering from pain, or which subject is suffering from sleep apnea or a CNS disorder which method comprises administering to the subject a therapeutically effective amount of a compound of claim 1 or a pharmaceutically acceptable salt or solvate thereof.

13. A process for the preparation of a compound of claim 1 which comprises reacting a compound of formula (II);

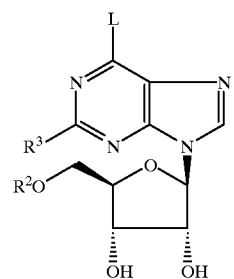 (II)
wherein L is a leaving group with a compound of formula $R^1NH_2$ or a salt thereof under basic conditions, $R^1$, $R^2$ and $R^3$ being as defined in claim 1.
14. A process for the preparation of a compound of claim 1 which comprises deprotection of a compound of formula (III);
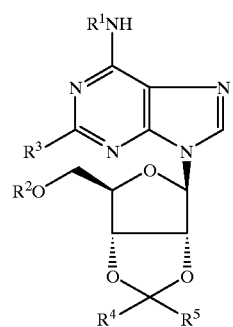 (III)
wherein $R^4$ and $R^5$ are each hydrogen or $C_{1-6}$alkyl.
* * * * *